United States Patent
Lopez et al.

(10) Patent No.: US 10,113,974 B2
(45) Date of Patent: Oct. 30, 2018

(54) ARRANGEMENT FOR THE SPECTROMETRIC MEASUREMENT OF PRODUCTS SUCH AS CEREALS, OLEAGINOUS PRODUCTS OR DERIVED PRODUCTS

(71) Applicant: Chauvin Arnoux, Paris (FR)

(72) Inventors: Eric Lopez, Gaillac (FR); Vincent Huret, Nanterre (FR)

(73) Assignee: CHAUVIN ARNOUX, Paris (FR)

( * ) Notice: Subject to any disclaimer, the term of this patent is extended or adjusted under 35 U.S.C. 154(b) by 0 days.

(21) Appl. No.: 15/322,476

(22) PCT Filed: Jun. 30, 2015

(86) PCT No.: PCT/FR2015/051792
§ 371 (c)(1),
(2) Date: Dec. 28, 2016

(87) PCT Pub. No.: WO2016/001572
PCT Pub. Date: Jan. 7, 2016

(65) Prior Publication Data
US 2017/0138864 A1    May 18, 2017

(30) Foreign Application Priority Data

Jul. 1, 2014 (FR) .................... 14 01552

(51) Int. Cl.
| | |
|---|---|
| *G01N 21/85* | (2006.01) |
| *G01N 21/3563* | (2014.01) |
| *G01N 21/359* | (2014.01) |
| *G01N 21/03* | (2006.01) |
| *G01N 21/13* | (2006.01) |

(Continued)

(52) U.S. Cl.
CPC ............ *G01N 21/85* (2013.01); *G01J 3/0237* (2013.01); *G01N 21/0303* (2013.01); *G01N 21/11* (2013.01); *G01N 21/13* (2013.01); *G01N 21/359* (2013.01); *G01N 21/3563* (2013.01); *G01N 33/10* (2013.01); *A01D 41/1277* (2013.01); *G01N 2021/0339* (2013.01); *G01N 2021/8466* (2013.01); *G01N 2021/8592* (2013.01); *G01N 2201/0633* (2013.01)

(58) Field of Classification Search
CPC ..................................................... G01N 21/85
USPC ........................................................ 356/72
See application file for complete search history.

(56) References Cited

U.S. PATENT DOCUMENTS

| | | |
|---|---|---|
| 3,242,739 A | 1/1963 | Botkin |
| 6,020,588 A | 2/2000 | Ditmarsen et al. |

(Continued)

FOREIGN PATENT DOCUMENTS

DE    1274821 B    8/1968

OTHER PUBLICATIONS

European Patent Office; Search Report in International Patent Application No. PCT/FR2015/051792 (dated Oct. 16, 2015).

*Primary Examiner* — Tarifur Chowdhury
*Assistant Examiner* — Omar Nixon
(74) *Attorney, Agent, or Firm* — Leydig Voit and Mayer

(57) ABSTRACT

An arrangement for the spectrometric measurement of products, such as cereals, oleaginous products, or derived products, includes a mechanism for selective adjustment of the position of a light beam in vertical and horizontal planes, and a selective adjustment device for ensuring that rays of the light beam are parallel.

15 Claims, 9 Drawing Sheets

(51) Int. Cl.
*G01N 21/11* (2006.01)
*G01N 33/10* (2006.01)
*G01J 3/02* (2006.01)
G01N 21/84 (2006.01)
A01D 41/127 (2006.01)

(56) References Cited

U.S. PATENT DOCUMENTS

2004/0233423 A1* 11/2004 Nakayama ......... G01N 21/0303 356/246
2007/0153282 A1 7/2007 Zubkov et al.
2013/0260405 A1* 10/2013 Nishino ............... G01N 21/645 435/23
2014/0111792 A1 4/2014 Claussen \* cited by examiner

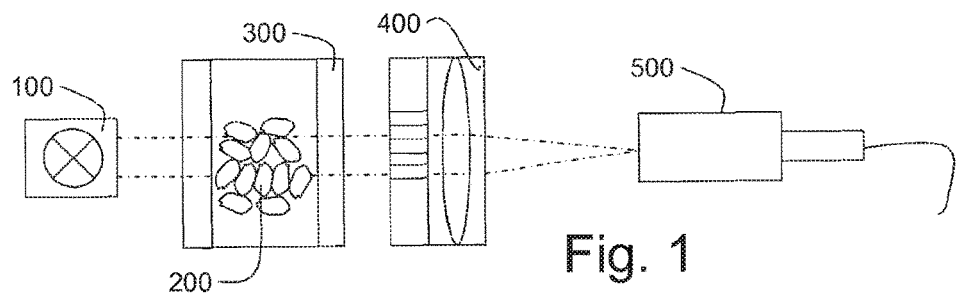
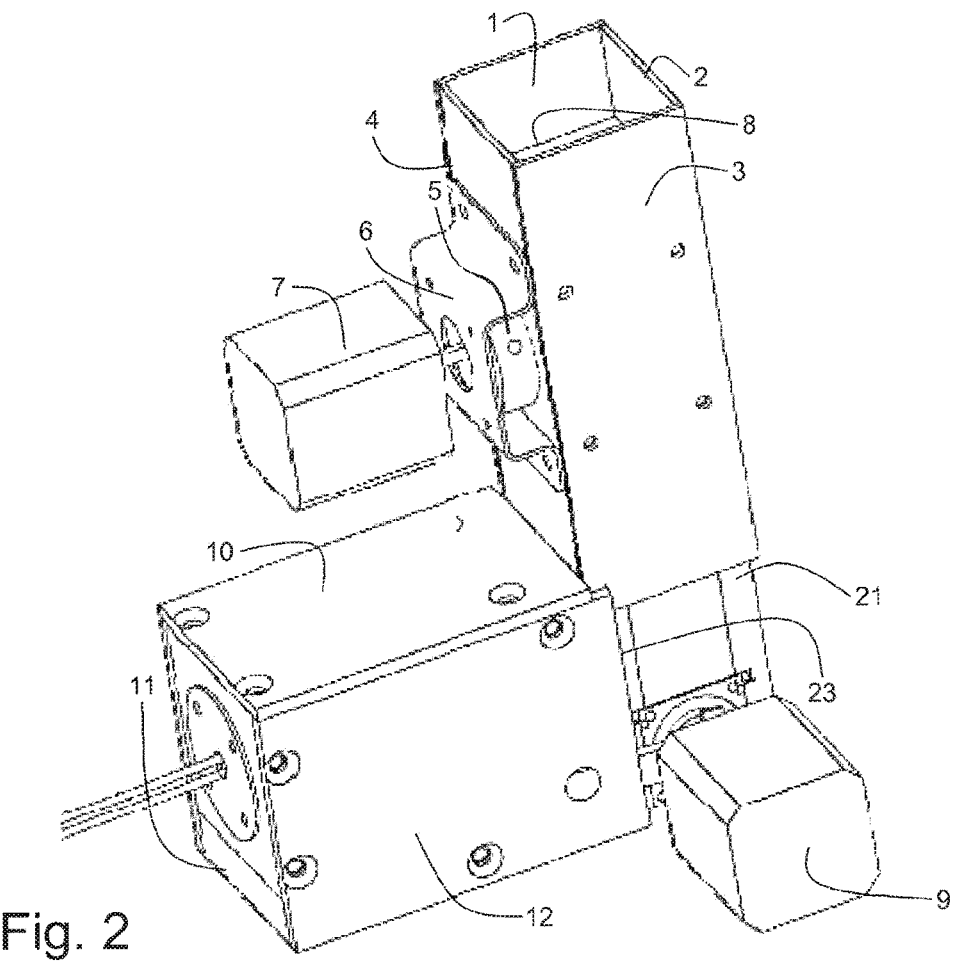

ARRANGEMENT FOR THE SPECTROMETRIC MEASUREMENT OF PRODUCTS SUCH AS CEREALS, OLEAGINOUS PRODUCTS OR DERIVED PRODUCTS

FIELD OF THE INVENTION

The present invention relates to a movable arrangement and a movable device for spectrometric measurement of cereals, oleaginous products or derived products.

BACKGROUND

It is known how to analyze cereal and oleaginous samples by spectrometric measurements in a near infrared mode, with view for example to determine their humidity, protein and oil percentage.

For this purpose, the sample is analyzed in the stationary state by means of analysis radiation by receiving a stabilized and collimated analysis radiation which is emitted by an emitter 100 positioned on one side of a readout chamber 300, before being received subsequently, via an optical diffraction system 400 by a receiver 500 located on the other side (FIG. 1).

The constraints on a movable spectroscopic measurement device for samples, lie in the requirement of perfect mechanical stability of the light source which should not deviate during possible vibrations and in the sequential flow of a constant volume sample in the readout chamber subject to the same vibrations. A regular flow of the sample allows regular homogeneity of the cereals. In the movable operation of such devices, it is difficult to find a remedy to the lack of natural homogeneity of the cereal or oleaginous sample in vibration. The grains which make up the sample are lightweight and different by their sizes. During its transport in a complex mechanism not adapted to the constraints of vibrations, the sample tends to be compacted, to no longer obey the laws of gravity by entanglement of the grains in a compact mass pressurized by the weight of the grains wainting above the others. Furthermore, the cereal varieties are different by their sizes, ranging from one millimeter in diameter for rapeseed to several millimeters for maize. Mechanically handling this size diversity in movement with a single mechanical system therefore proves to be difficult.

Another problem is having a correctly aligned light and having parallel rays for an analyzing of the sample which is flowing, in order to obtain consistent and accurate measurements. During a possible transport and/or vibrations, the alignment of the light tends to be maladjusted, the flow tending to not occur under a constant volume and the grains tending to be compacted and no longer being emptied from the device. Now, up till now, no satisfactory solution to this problem has been found.

SUMMARY OF THE INVENTION

In order to attain this goal, the arrangement according to the invention is characterized in that it comprises a selective adjustment mechanism of the position of the light beam in vertical and horizontal planes and a selective adjustment device for ensuring that the rays of the light beam are parallel.

Preferably, the obturation and opening device comprises a rotary cylinder in the bottom of the tank of the product and which comprises a bore for letting through the product and in that the bore in its open position forms a predetermined angle α with respect to the horizontal direction so as to form a tilted ramp for sliding of the product flowing in the readout chamber, in order to ensure the homogeneity of the product in the chamber.

Advantageously, the tilt angle α is specific for different types of products.

Advantageously, the amount of the product flowing into the readout chamber is established by the opening time of the obturation and opening device.

Further, the obturation device is able to oscillate around its opening position by a predetermined oscillation angle in order to further improve the homogeneity of the product in the readout chamber.

Preferably, the mechanism for adjusting the position of the light beam comprises a device bearing the light source, and includes a plurality of adjustment plates, two of which are pivoting around respectively vertical and horizontal axes by means of screws which may be actuated from the outside.

Advantageously, a first plate is pivotally mounted on the supporting plate around a horizontal or vertical axis under the effect of screws crossing the supporting plate in order to bear through their internal ends on the face opposite to the first plate, while the second plate bearing the light source is pivotally mounted around a vertical or horizontal axis on the first plate under the effect of screws crossing the supporting plate and the first plate for bearing against the face opposite to the second plate.

Advantageously, each plate may be oriented with two screws, one of which is used for adjustment and the other ensures the maintaining of the plate in its adjusted position.

Preferably, the plate axes are formed each with two screws radially penetrating into the periphery of the corresponding plate and which are used, after the adjustment, as means for blocking the plates in their adjusted position.

Further, the arrangement of the invention comprises an optical block comprising a focusing member which may be moved manually on the optical axis so that the light source is positioned in the focal point of the focusing member.

Advantageously, the optical member is screwed in its support and axially movable by manual rotation.

BRIEF DESCRIPTION OF DRAWING FIGURES

The invention will be better understood, and other objects, features, details and advantages thereof will become more clearly apparent in the explanatory description which follows, made with reference to the appended schematic drawings only given as an example illustrating an embodiment of the invention and wherein:

FIG. 1 is a schematic view which illustrates the principle of a cereal spectrometric measurement arrangement or the like;

FIG. 2 is a perspective view of an arrangement according to the invention;

Figure 12:
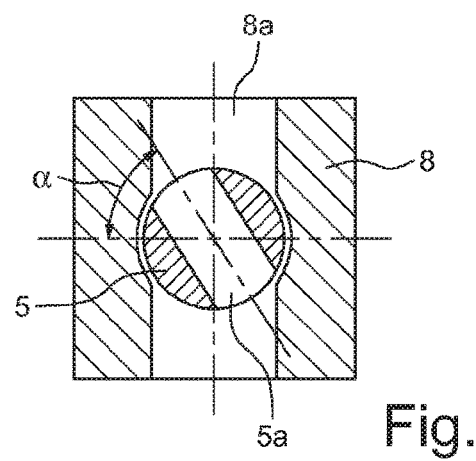
Figure 5:
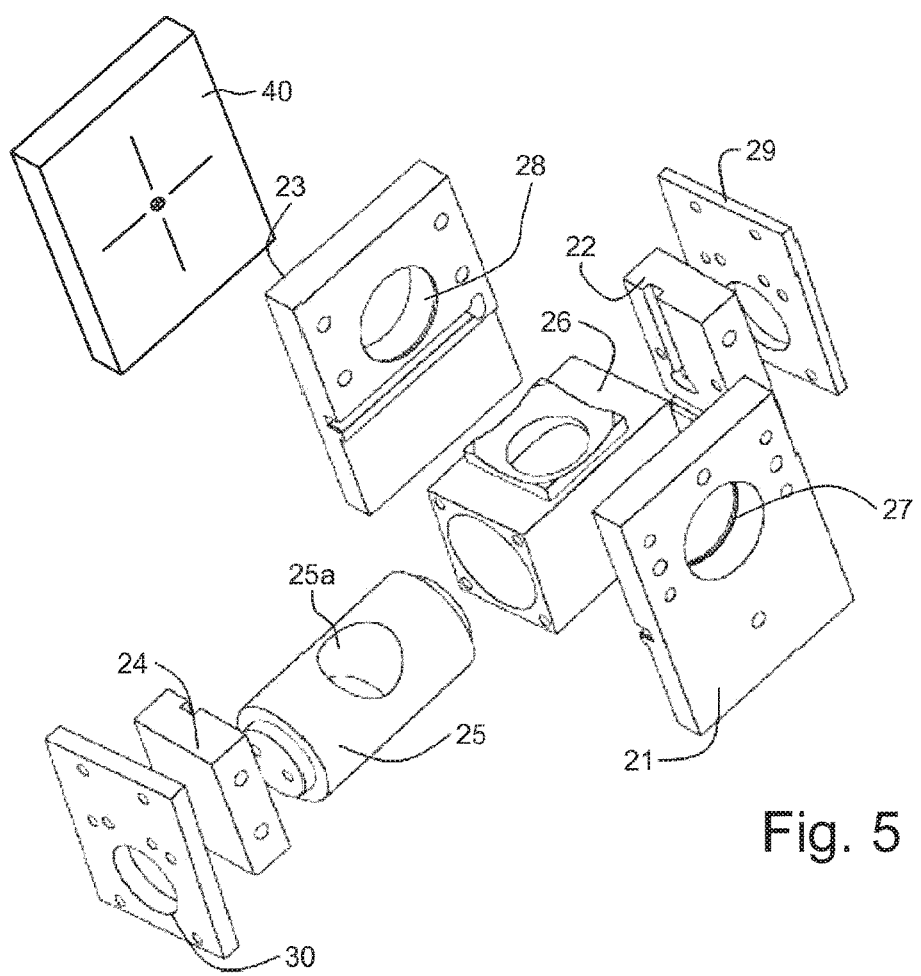
FIG. 5 is a perspective and exploded view of a second sub-set according to the invention indicated in II in FIG. 3.
Figure 6:
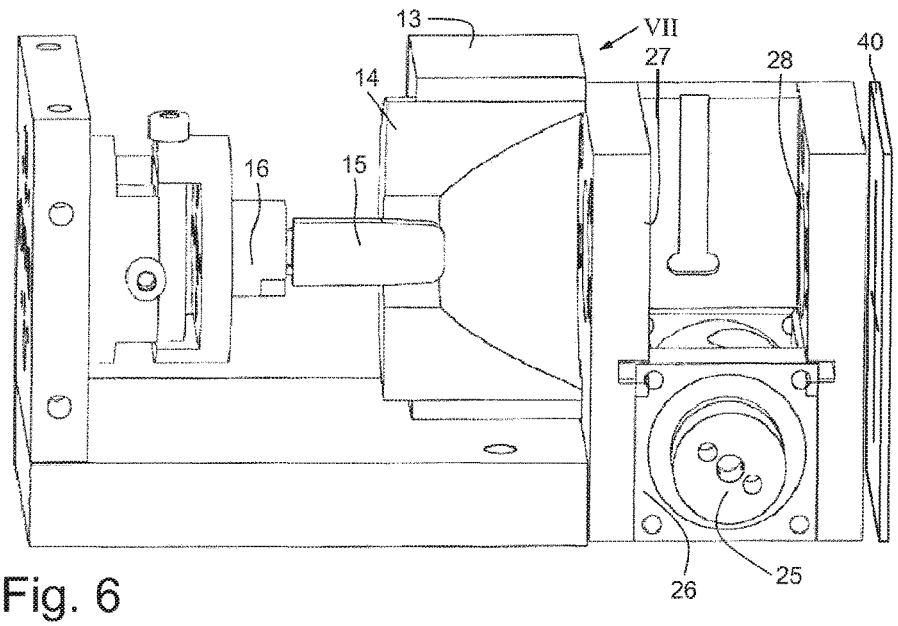
FIG. 6 is a view showing a third sub-set of an optical block according to the invention, indicated in III of FIG. 3 and placed adjacent to the sub-set II.
Figure 7:
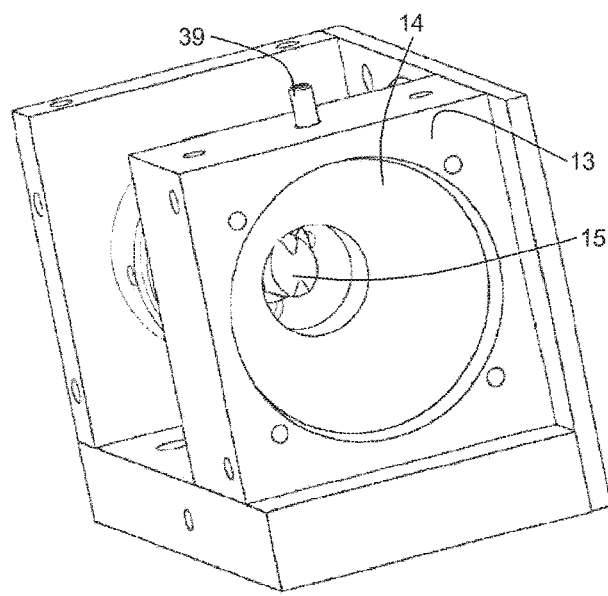
FIG. 7 is a perspective view and at a larger scale of the portion indicated in VII in FIG. 6.
Figure 8A:
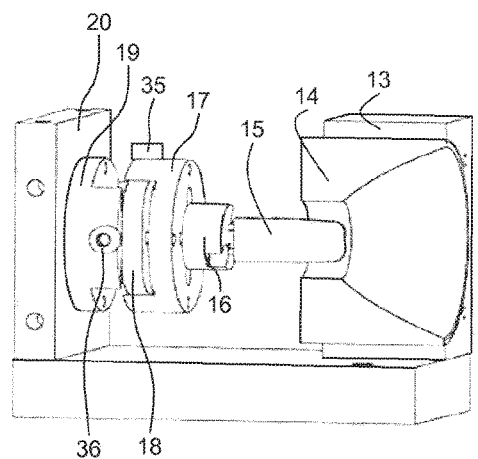
Figure 8B:
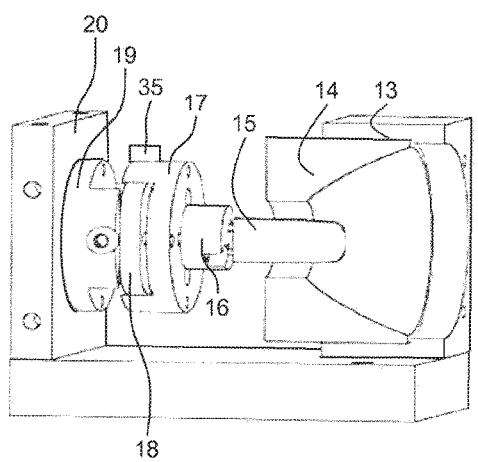
Figure 9A:
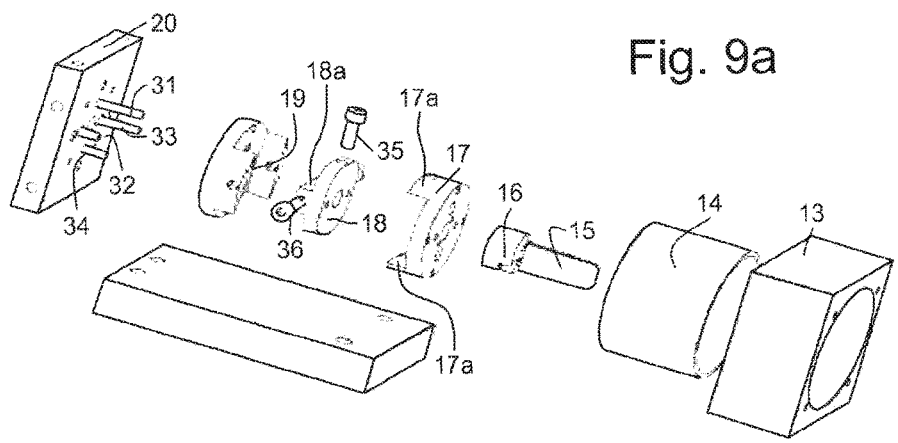
Figure 9B:
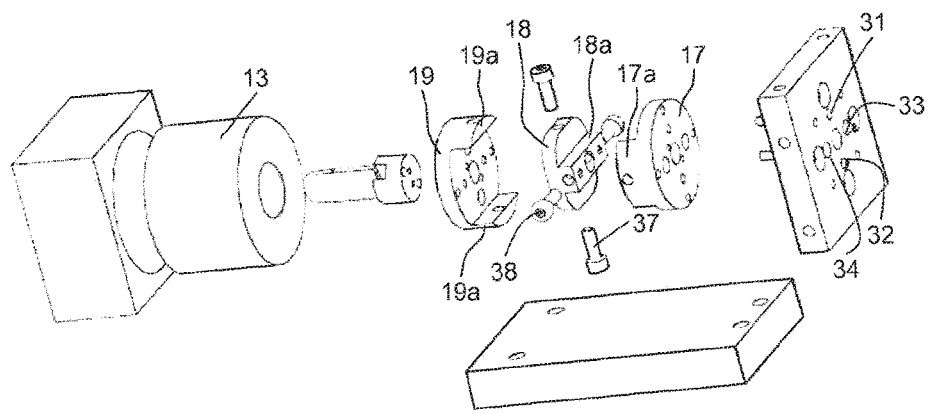
Figure 10A:
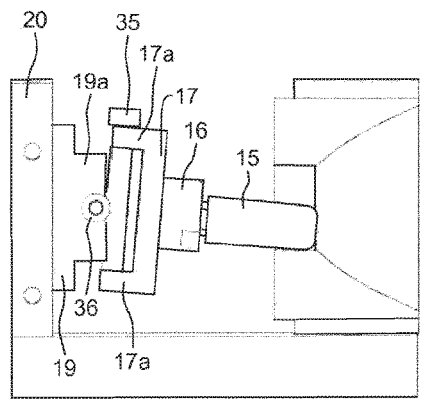
Figure 10B:
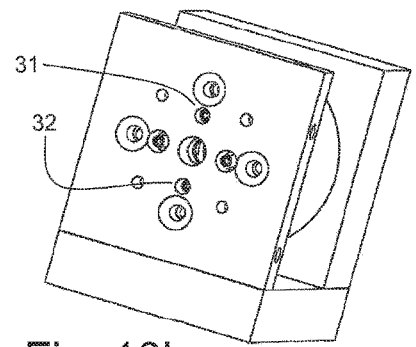
Figure 10C:
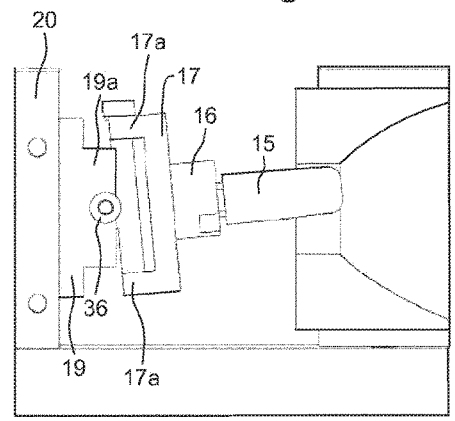
Figure 10D:
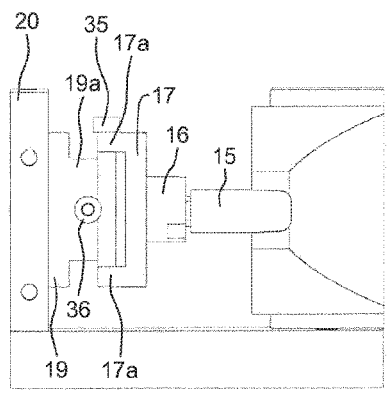
Figure 11A:
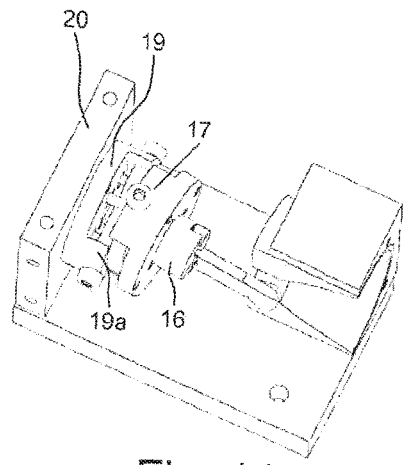
Figure 11B:
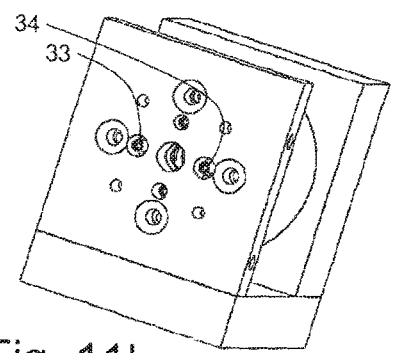
Figure 11C:
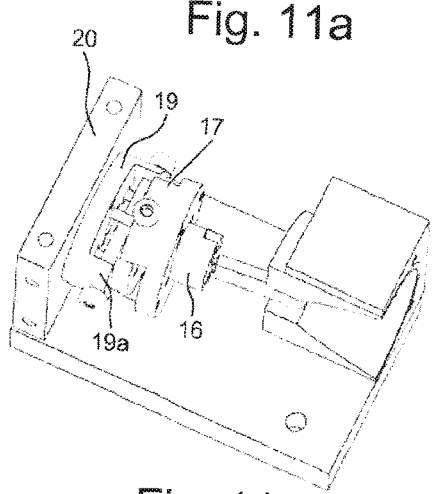
Figure 11D:
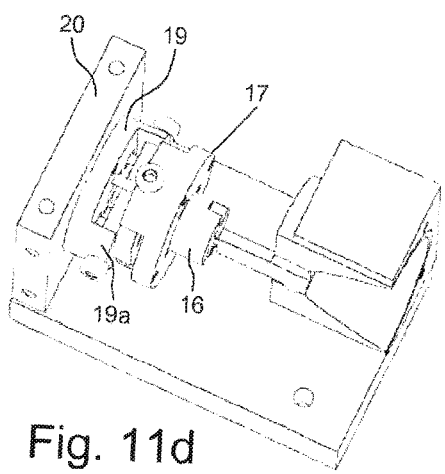

FIGS. 8*a* and 8*b* are two perspective views of the adjustment mechanism of the lamp, according to the invention;

FIGS. 9a and 9b are two perspective and exploded views of the adjustment mechanism for the position of the lamp;

FIGS. 10a, 10b, 10c, and 10d and 11a, 11b, 11c, and 11d illustrate the method for positioning the analysis light source in the optical axis;

FIG. 12 is a schematic view illustrating the device of the invention for ensuring homogeneity of the flow of the grains in the readout and analysis chamber.

DETAILED DESCRIPTION

Figure 3:
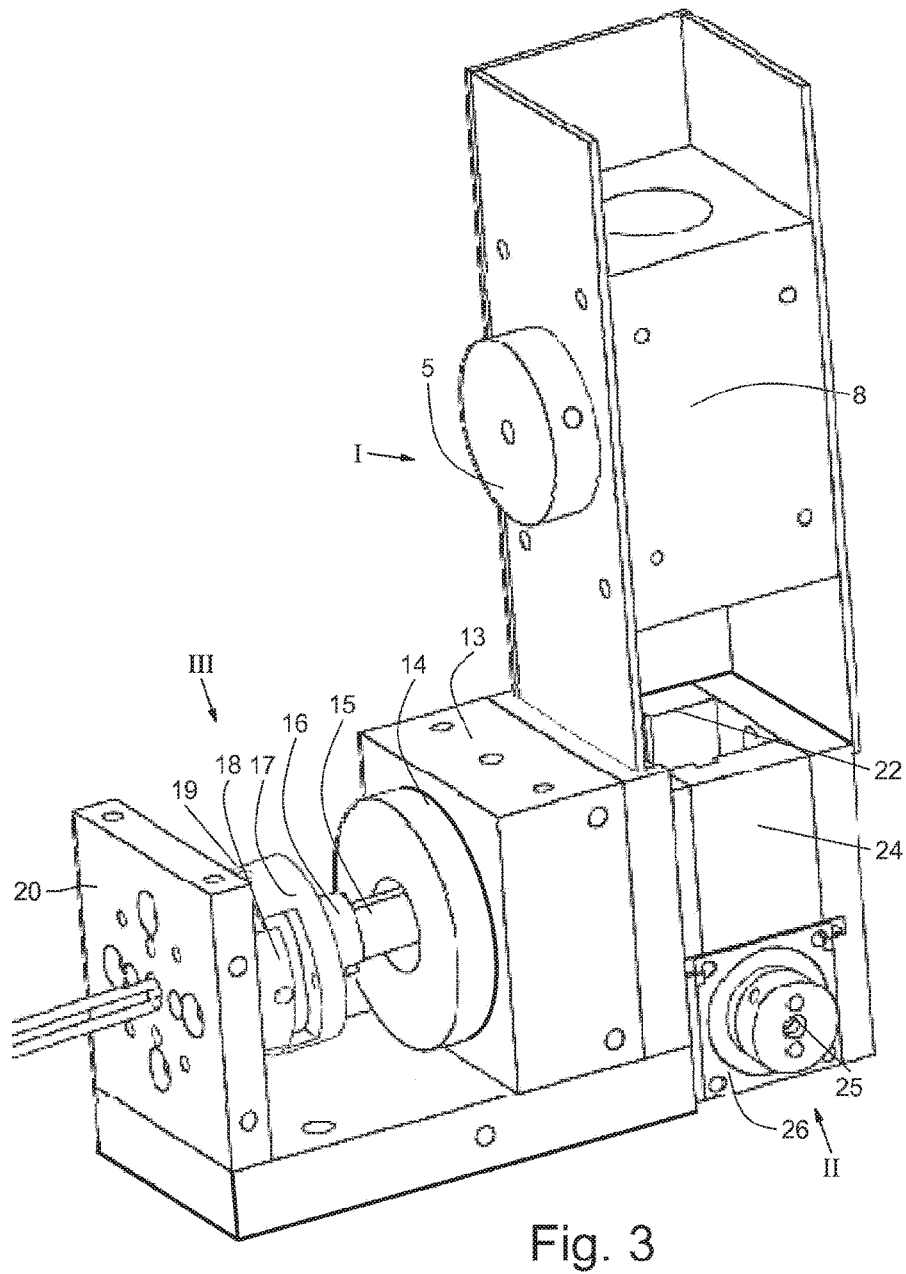
FIG. 3 is another perspective view of the arrangement according to the invention.
Figure 4:
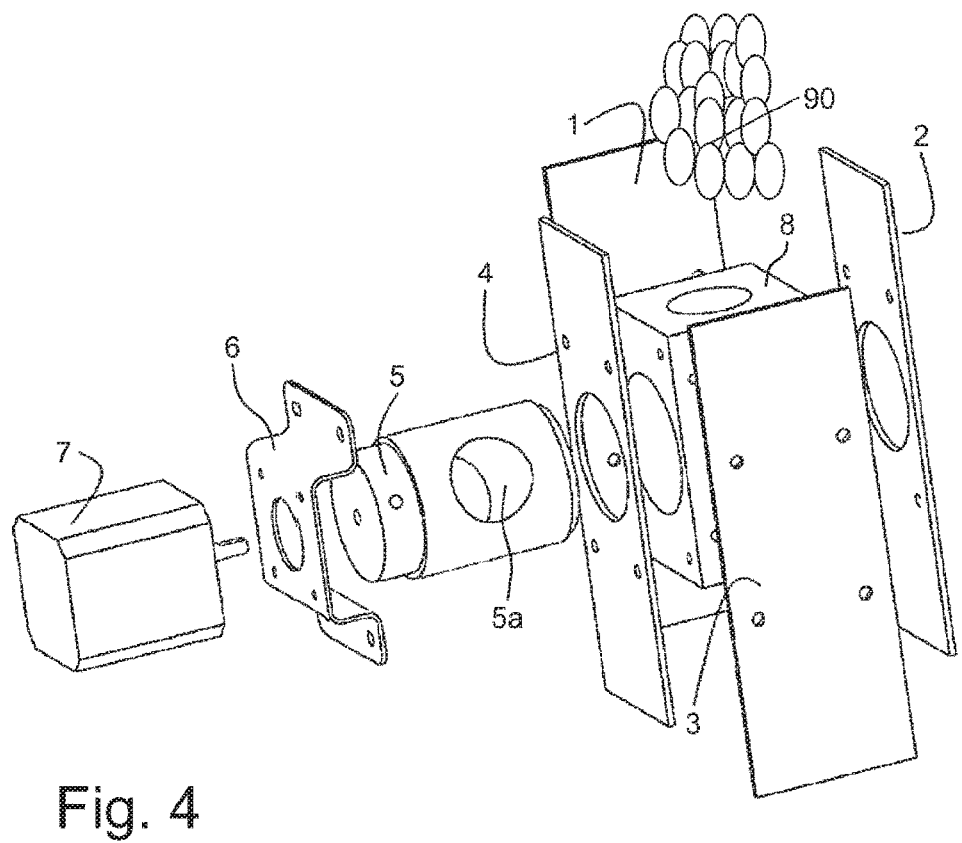
FIG. 4 is a perspective and exploded view of the sub-set indicated in I in FIG. 3.

As shown in FIGS. 2 and 3, the arrangement for spectrometric measurement of oleaginous cereals or derived products, according to the invention comprises three sub-sets, i.e., a first sub-set I intended to ensure flow of the grains to be analyzed in the readout and analysis chamber, a second sub-set II including the readout chamber and the device for discharging the grains and a third sub-set III which forms the optical block of the arrangement.

The first sub-set I comprises a casing with a parallelepipedal shape consisting of the walls 1, 2, 3, and 4, delimiting a chamber for supplying grains as this is indicated schematically, and below a supporting body 8 axially crossed from top to bottom by a cylindrical bore 8a, and an obturation cylinder 5 positioned in the support 8, perpendicular to the axis of the bore 8a, provided with a cylindrical through-bore 5a and rotary between a position in which the bore 5a allows the letting through of the grains into the readout chamber and a position for obturating the bore 8a and therefore for closing the supply chamber. The obturation cylinder 5 may be manually actuated or driven into rotation by a motor 7 mounted on the side wall 4 by means of a bracket 6.

The second sub-set II includes the chamber for reading out a sample and delimited by a parallelepipedal casing consisting of the walls 21, 22, 23, and 24. The readout chamber is crossed by the light beam for reading and analyzing. For this purpose, the walls 21 and 23 have windows 27, 28 for letting through the beam. Below the chamber is positioned a cylindrical support 26 which forms the bottom of the readout chamber. In this support 26 is rotatably mounted a rotary obturation cylinder 25 which may be actuated manually or driven into rotation by a motor 9. The obturation cylinder 25 is rotary between a position in which a cylindrical drilled hole 25a open into the readout chamber and allows discharge of the grains having been analyzed, and an angular position in which the cylinder 25 obturates the bottom of the chamber because the drill hole is oriented perpendicularly.

The third sub-set III is an optical block comprising a parallelepipedal casing formed by walls 10, 11, 12 which contain an optical device including a parabolic reflector support 13, a parabolic reflector 14 and a lamp 15 provided with a socket 16 mounted on adjustment plates 17, 18 and 19, as well as a supporting plate 20. Alternatively, the optical device comprises a lens support and a lens instead and in the place of the parabolic reflector support 13 and of the parabolic reflector 14. The plates 17 and 18 may be oriented by means of screws 31 to 34, screwed into the plate 20 which they cross and which may be actuated from the outside. These screws also cross the plate 19 so as to be able to bear in their internal ends upon the plates 17 and 18; by actuating these screws 11, it is possible to adjust, by means of these screws the position of the lamp 15 in a way which will be described further on.

It should be noted that the plate 19, as this is seen in FIGS. 10a to 10d and 11a-11d bears upon the internal face of the plate 20. It includes two protrusions 19a which are located diametrically opposite to the periphery of the plate and each crossed by a screw 36 which penetrates into a diametrical rib 18a on the face of the plate 18, which is opposite to the plate 19. The plate 17 includes at its periphery protrusions 17a also diametrically opposite but shifted to the protrusions 19a of the plate 19 by an angle of 90°. These protrusions 17a are crossed by screws 35 which penetrate into the periphery of the plate 18. As regards the lamp 15, it is attached through its socket 16 on the free front face of the plate 17. The screws 35 and 36 form the pivot axes of the plates 17 and 18 and give the possibility, after the adjustment, of blocking the plates in their adjusted positions.

The plates 17, 18, 19 form the vertical and horizontal adjustment and supporting mechanism of the lamp 15, i.e. of the light source, in this case of the filaments of the lamp. This mechanism gives the possibility of positioning the source in a simple way in the optical axis of the optical block. The correct positioning may be verified for example by means of a projection screen schematically indicated in 40 on which a cross specifies the position of the optical axis.

For adjusting the beam, so that these rays are parallel, the parabolic reflector is movable along the optical axis. For this purpose, the reflector is screwed in its support. Thus, the rotation of the reflector allows its displacement in the optical axis until the source, i.e. in the present case, the filaments of the lamp, are found in a focal point of the reflector.

As regards the positioning of the source in the optical axis first of all in the vertical plane, the screw 31 or the screw 32 is screwed against the face opposite to the plate 18, the screws 36 being used as pivot axes, if the screw 31 is actuated, the screw 32 allows blocking of the plate in its adjusted position. If the screw 32 is the one which is actuated, it is the screw 31 which maintains the plate blocked in its adjusted position.

In order to position properly the beam in the horizontal plane, the screw 33 or the screw 34 are actuated. These screws cross the plate 18 in order to bear through their ends against the face opposite to the plate 17. The screws 38 then form the vertical pivot axes. After adjusting the positions of the plate 17 and 18, the screws which form the pivot axes give the possibility of blocking the plates in their adjusted position.

It is seen that the mechanism for positioning the beam in the optical axis is very simple and easy to handle.

According to another advantageous feature of the invention, the latter gives the possibility of ensuring in a very simple way the homogeneity of the grains in the measurement chamber.

Indeed, the homogeneity is ensured by means of the obturation cylinder 5 which is rotary in its support 8 for obturating the supply chamber or the opening allowing flow of the grains into the readout or measurement chamber. Now, in its open position, the bore 5a is not oriented vertically, but is only tilted relatively to the horizontal axis by a predetermined angle. Thus, the wall of the bore forms a ramp for sliding the grains which singled out them and avoids their agglomeration.

The tilt angle is specific for the different types of grains. For example, for wheat the angle is 60°, for rapeseed only 15°. The amount of grains in the measurement chamber is also specific to the different types of grains and it is determined by the opening time.

In order to further improve the homogeneity of the grains in the measurement chamber, it may be ensured that the rotary cylinder 5 oscillates around its opening angle by a few predetermined degrees, for example two degrees. By using a stepping motor for rotating the cylinder, the oscillation angle may easily be formed and adjusted.

Of course multiple modifications may be brought to the embodiment described and illustrated as a non-limiting example. Thus, instead of using a parabolic reflector, it is also possible to use a suitable focusing lens.

The invention claimed is:

1. A spectrometric measurement arrangement for analysis of a sample of a product, the spectrometric measurement arrangement comprising:
    a light source for producing a light beam;
    a readout chamber crossed by the light beam for analyzing the sample of the product that is located in the readout chamber;
    a tank for containing the product to be analyzed;
    a feeding device feeding the product from the tank and into the readout chamber, wherein the feeding device is movable between an obturating position, preventing flow of the product from the tank and into the readout chamber, and an open position allowing flow of the product from the tank and into the readout chamber, for controlling amount of the product flowing into the readout chamber;
    a discharge device for discharging the product from the readout chamber;
    a selective adjustment mechanism for adjusting position of the light beam in two mutually orthogonal planes, wherein the selective adjustment mechanism comprises
    a device bearing the light source,
        a plurality of adjustment plates, wherein first and second adjustment plates of the plurality of the adjustment plates pivot around respective first and second mutually orthogonal axes, and
        a plurality of adjustment screws actuated from outside the readout chamber for pivoting the first and second adjustment plates around the respective first and second mutually orthogonal axes; and
    a selective adjustment device for ensuring that rays of the light beam are parallel to each other along an optical axis.

2. The arrangement according to claim 1, wherein the feeding device comprises a rotary cylinder located in a bottom of the tank and including a bore for passage of the product from the tank and into the readout chamber, and
    the bore, in the open position of the feeding device, forms a tilt angle which is not horizontal, as a tilted ramp, for sliding of the product into the readout chamber.

3. The arrangement according to claim 2, wherein the tilt angle is different for different products.

4. The arrangement according to claim 3, wherein the amount of the product flowing into the readout chamber from the tank is established by how long the feeding device is in the open position.

5. The arrangement according to claim 2, wherein the feeding device may oscillate with respect to the open position by an oscillation angle.

6. The arrangement according to claim 1, wherein
    a third plate of the plurality of adjustment plates is a supporting plate,
    the first plate is pivotally mounted on the supporting plate for pivoting around the first axis in response to turning of a first adjustment screw of the plurality of adjustment screws, and the first adjustment screw traverses and engages the supporting plate and bears upon a face of the first plate, and
    the second plate bears the light source and is mounted to pivot around the second axis in response to turning of a second adjustment screw of the plurality of adjustment screws, and the second adjustment screw traverses and engages the supporting plate and the first plate and bears against a face of the second plate.

7. The arrangement according to claim 6, wherein
    each of the first and second adjustment screws includes a respective pair of adjustment screws of the plurality of adjustment screws,
    a first adjustment screw of each pair of adjustment screws is used for adjusting position of the light beam, and
    a second adjustment screw of each pair of adjustment screws is used to maintain the respective plate in an adjusted position.

8. The arrangement according to claim 1, including a plurality of mounting screws, wherein
    the first and second mutually orthogonal axes about which the first and second adjustment plates pivot are defined by respective mounting screws of the plurality of mounting screws,
    the respective mounting screws radially penetrate into peripheries of the respective first and second adjustment plates, and
    the respective mounting screws are used, after adjustment of positions of the first and second adjustment plates with respective adjustment screws, to maintain the first and second adjustment plates in position.

9. The arrangement according to claim 1, wherein the selective adjustment device includes a focusing member having a focal point and may be displaced manually, along the optical axis, so that the light source is positioned at the focal point of the focusing member.

10. The arrangement according to claim 9, including an optical member support, wherein
    the focusing member threadedly engages the optical member support, and
    the focusing member is axially displaceable by rotation relative to the optical member support.

11. A spectrometric measurement arrangement for analysis of a sample of a product, the spectrometric measurement arrangement comprising:
    a light source for producing a light beam;
    a readout chamber crossed by the light beam for analyzing the sample of the product that is located in the readout chamber;
    a tank for containing the product to be analyzed having a bottom end through which the product is discharged, wherein the tank includes, proximate the bottom, a bore having a control axis transverse to flow of the product out of the bottom of the tank;
    a feeding device feeding the product from the tank and into the readout chamber, wherein
        the feeding device includes a rotating cylinder disposed within the bore and rotatable about the control axis between an obturating position, preventing flow of the product from the tank and into the readout chamber, and an open position allowing flow of the product from the tank and into the readout chamber, for controlling amount of the product flowing into the readout chamber,
        the rotating cylinder includes a through hole extending transverse to the control axis for passage of the product from the tank and into the readout chamber when the rotating cylinder is in the open position, and the through hole, when the rotating cylinder is in the open position, forms a tilt angle which is not horizontal, as a tilted ramp for sliding of the product into the readout chamber, and the tilt angle may be varied by degree of rotation of the rotating cylinder depending on the product being fed from the tank into the readout chamber;

a discharge device for discharging the product from the readout chamber;

a selective adjustment mechanism for adjusting position of the light beam in two mutually orthogonal planes; and a selective adjustment device for ensuring that rays of the light beam are parallel to each other along an optical axis.

12. The arrangement according to claim 11, wherein the amount of the product flowing into the readout chamber from the tank is established by how long the rotating cylinder is in the open position.

13. The arrangement according to claim 11, wherein the feeding device may oscillate with respect to the open position by an oscillation angle.

14. The arrangement according to claim 11, wherein the selective adjustment device includes a focusing member having a focal point and may be displaced manually, along the optical axis, so that the light source is positioned at the focal point of the focusing member.

15. The arrangement according to claim 14, including an optical member support, wherein the focusing member threadedly engages the optical member support, and the focusing member is axially displaceable by rotation relative to the optical member support.

* * * * *